United States Patent [19]

Behnke et al.

[11] Patent Number: 5,573,921
[45] Date of Patent: Nov. 12, 1996

[54] IMMUNOCHEMICAL DISPLACEMENT FOR DETERMINING AN ANALYTE

[75] Inventors: Andreas Behnke, Bad Schwartau; Andreas Manns, Lübeck; Thomas Wuske, Malente; Klaus P. Rindt, Lübeck, all of Germany

[73] Assignee: Drägerwerk Aktiengesellschaft, Lübeck, Germany

[21] Appl. No.: 111,727

[22] Filed: Aug. 25, 1993

[30] Foreign Application Priority Data

Sep. 4, 1992 [DE] Germany ............... 42 29 591.2

[51] Int. Cl.$^6$ ............... G01N 33/543; G01N 33/558
[52] U.S. Cl. ............... 435/7.92; 422/56; 435/7.93; 435/7.94; 435/970; 436/501; 436/514; 436/518
[58] Field of Search ............... 435/7.9, 7.92, 435/7.93, 7.94, 7.95; 436/501, 514, 517, 518, 524, 525, 528, 533; 422/56, 57, 60; 935/970

[56] References Cited

U.S. PATENT DOCUMENTS

| | | |
|---|---|---|
| 3,964,871 | 6/1976 | Hockstrasser . |
| 4,434,236 | 2/1984 | Freytag ............... 436/512 |
| 4,803,170 | 2/1989 | Stanton et al. ............... 436/518 |
| 4,895,809 | 1/1990 | Schlabach et al. ............... 436/518 |
| 4,956,275 | 9/1990 | Zuk et al. ............... 435/288 |
| 5,073,484 | 12/1991 | Swanson et al. ............... 435/7.92 |
| 5,183,740 | 2/1993 | Ligler et al. ............... 435/7.32 |
| 5,229,073 | 7/1993 | Luo et al. ............... 422/56 |
| 5,340,748 | 8/1994 | Baugher et al. ............... 436/518 |

FOREIGN PATENT DOCUMENTS

| | | |
|---|---|---|
| 0191640 | 2/1986 | European Pat. Off. . |
| 2204398 | 11/1088 | United Kingdom . |
| W091/13354 | 9/1991 | WIPO . |

OTHER PUBLICATIONS

B. K. Van Weemen et al, in G Feldmann et al (Eds.) Immuno Enzymatic Techniques, Inserm Symposium 2, North Holland Publishing Company, 1976, pp. 125–133.

A. J. Pesce et al, *Scand. Journ. Immunol.* 8, Suppl. 7, 1–6, 1978.

*Primary Examiner*—David Saunders
*Attorney, Agent, or Firm*—McGlew and Tuttle, P.C.

[57] ABSTRACT

The present invention pertains to a process for determining an analyte, especially a low-molecular-weight pollutant in a sample. It is carried out by partially dipping into the sample a test strip, on which antibodies which are specific for the analyte and to which in turn a tracer is bound, are immobilized. During the capillary migration of the sample through the test strip, the analyte partially displaces the tracer. The tracer that has remained on the antibody is subsequently visualized by, e.g., dyeing. The intensity of the dyeing is an indicator of the amount of analyte detected.

13 Claims, 10 Drawing Sheets

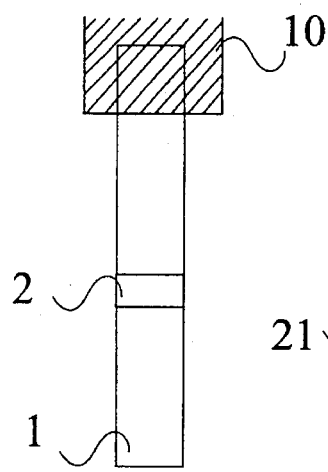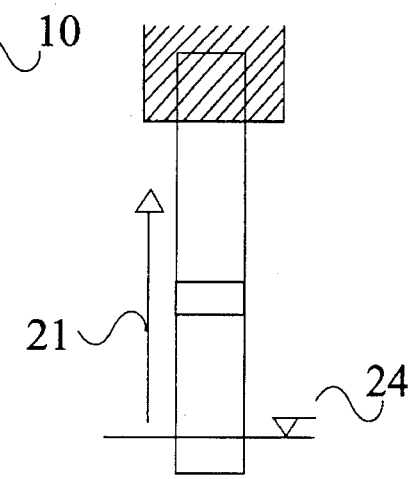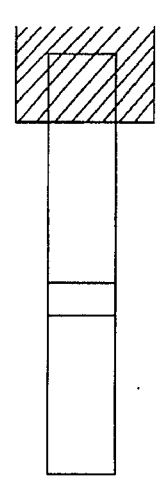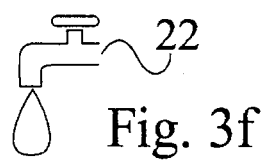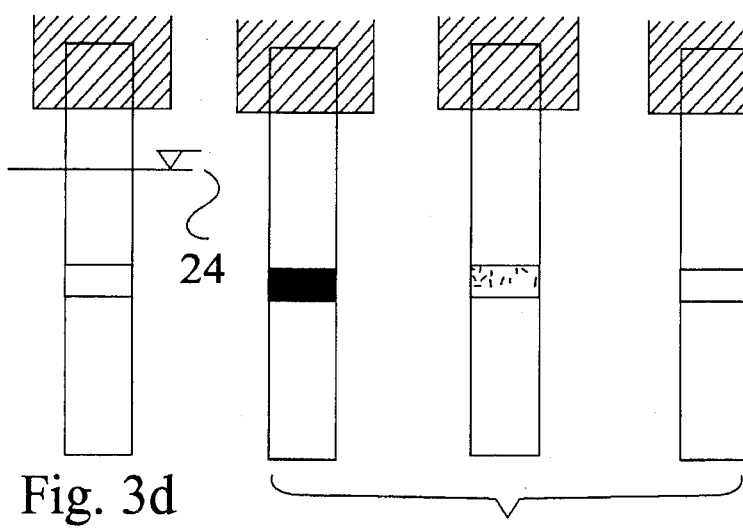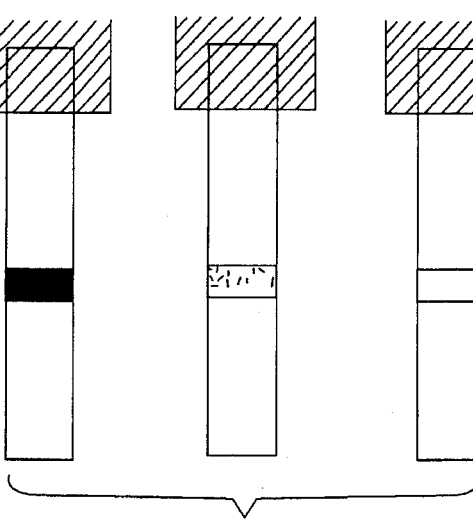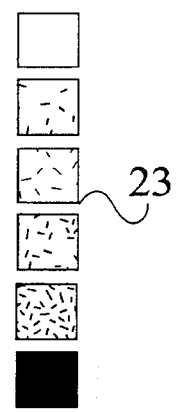

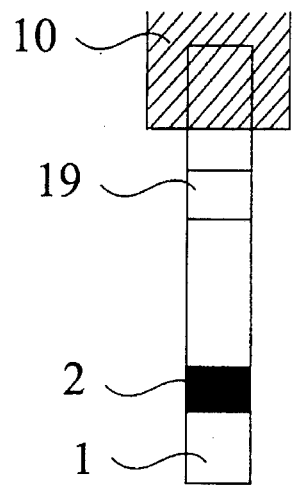 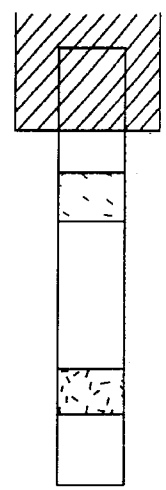 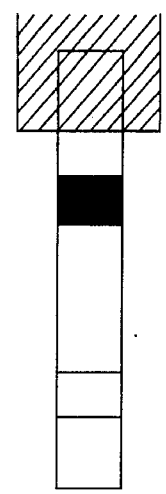 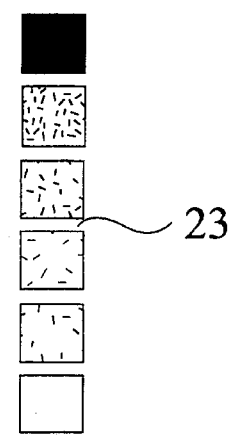
Fig. 8a　　Fig. 8b　　Fig. 8c　　Fig. 8d
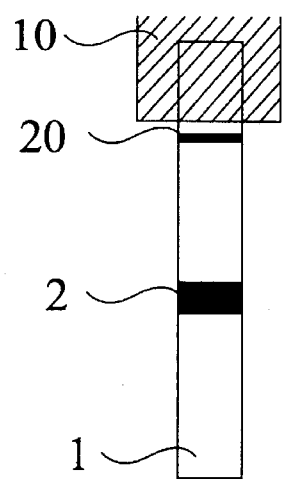 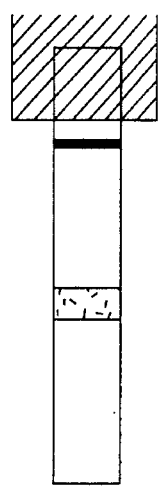 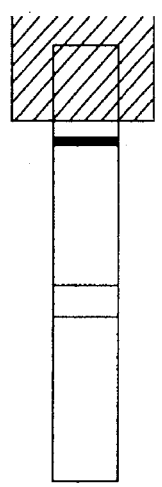 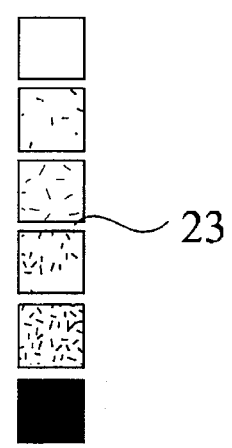
Fig. 9a　　Fig. 9b　　Fig. 9c　　Fig. 9d

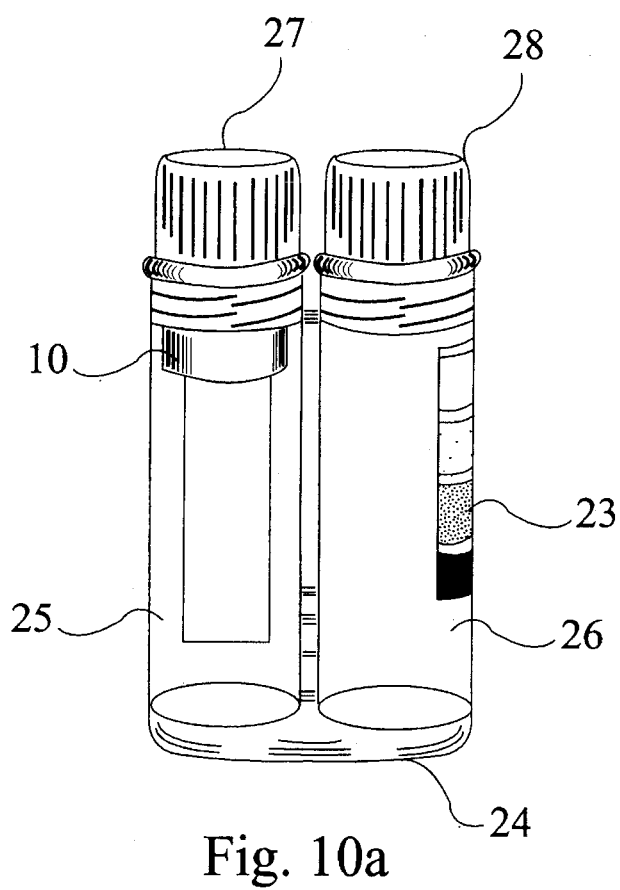
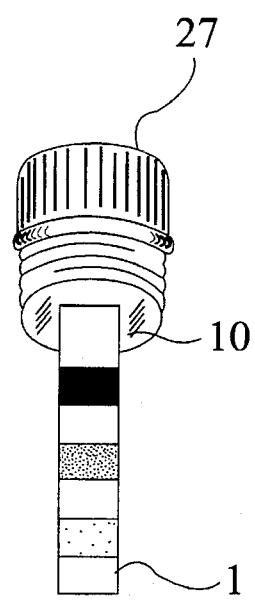
Fig. 10a
Fig. 10b

IMMUNOCHEMICAL DISPLACEMENT FOR DETERMINING AN ANALYTE

FIELD OF THE INVENTION

The present invention pertains to an immunological process for determining an analyte, as well as to a device for carrying out the process wherein a test strip formed of an absorbent material is used, on which an antibody is immobilized in at least one partial or measurement area, the process involving bringing into contact of a test solution, which contains the sample and another reaction partner one end of the test strip, allowing the test solution to pass over at least one part of the test strip, including the partial or measurement area containing the antibody, by capillary migration, washing the test strip, bringing the test strip in a contact with a developing solution that contains members of a signal-generating system that is able to generate a detectable signal as a function of the amount of analyte in the sample in the partial area containing the antibody and comparison of the signal generated with a comparison standard.

BACKGROUND OF THE INVENTION

Analytes also include, among other things, low-molecular-weight pollutants, e.g., pesticides and their decomposition products (metabolites). These pollutants may also be contained in aerosols.

In recent years, public discussion has increasingly frequently focussed on the use of synthetic pesticides for the purpose of plant protection and the environmental pollution associated with it. The European Drinking Water Ordinance, the "EC Guidelines for the Quality of Water for Human Consumption," as well as the MAC Values List (the MAC value is the maximum allowable concentration of a working substance in the form of a gas, vapor or suspended matter in air at the workplace) specify limit values for these substances. The limit value is, e.g., 0.1 µg per L of water for certain substances. The detection limit should be below this value by one to two orders of magnitude for accurate analysis. The large number of substances in question and the low limit values represent a big problem for physical and chemical analysis.

Physical and chemical analytical methods require complicated enrichment processes, are highly expensive, time-consuming, and can be carried out only by specialized skilled technicians in specially equipped laboratories. To avoid the above-mentioned disadvantages, immunological processes—which have already been used routinely in clinical diagnostics for the detection of a great variety of substances—have recently been developed, especially for the quantitative and qualitative determination of pollutants in soil, water, or air samples (e.g., West German Offenlegungsschrift No. DE-OS 40 13 004). DE-OS 40 13 004 describes a classical immunochemical method, used for low molecular weight organic substances, e.g. haptens, encountered in the field of analytical methods for pollution control. To this effect, DE-OS 40 13 004 proposes to use an antibody-enzyme-conjugate in conjunction with a competitive immunoassay.

Immunoassays are highly sensitive test systems for the qualitative and/or quantitative determination of substances on the basis of the antibody-antigen reaction, wherein the substance to be detected (analyte) acts as an antigen. The antibodies are first induced by immunizing laboratory animals, and are subsequently isolated according to conventional methods. These so-called "polyclonal" antibodies are highly heterogeneous in terms of both their specificity and affinity with respect to the analyte and their association with the individual classes of immunoglobulins. Instead of individual immunized animals, it is also possible to use hybrid somatic cell lines (hybridomas) as the source for so-called "monoclonal" antibodies (mAbs) against very specific antigens (=analytes).

The advantages of monoclonal antibodies over polyclonal antibodies are numerous, e.g., a) monoclonal antibodies (mAbs) can be obtained in large amounts and at a high degree of purity;

b) the mAbs are homogeneous in terms of the antigen reactivity, and their properties are the same in each batch prepared;

c) hybridoma cell lines which produce mAbs can be stored for several years, without losing their specific properties.

Monoclonal antibodies are therefore preferably, but not exclusively, used for the present invention.

The antigen-antibody binding is used for detecting a pollutant in immunoassays. The same intermolecular forces are responsible for the formation of the antigen-antibody complexes both in vivo and in vitro. They are based on the attraction of groups carrying opposite charges, on the interaction between hydrophilic and hydrophobic groups, as well as on the van der Waals forces, which originate from the interactions between electron clouds. All these interactions or bindings are, in principle, reversible and non-covalent, and the forces exert their effect only when the antibody and antigen come very close to each other.

Homogeneous and heterogeneous systems are distinguished in the immunoassays. In the homogeneous system, the enzyme activity, e.g., that of a hapten-enzyme conjugate, is influenced by the antigen-antibody reaction and is measurable. Washing and separation steps are not necessary. Systems in which the enzymatic activity of the conjugate is not influenced require one or more separation or washing steps, and are therefore called heterogeneous tests. The heterogeneous immunoassays include, e.g., competitive assays. Such test methods involve, in general, the competition between a known amount of labeled analyte and an unknown amount of unlabeled analyte to be determined for a limited amount of an analyte-specific, solid phase-bound partner of an immunological reaction. The solid phase-bound, labeled analyte can be separated from the free, labeled analyte after the reaction, and its amount can be determined chemically or physically on the basis of the labeling. The measured value is inversely proportional to the amount of the unlabeled analyte to be determined. As an alternative, it is also possible to determine the amount of the labeled analyte that has remained non-bound. The measured value is directly proportional in this case to the amount of the analyte to be determined. Examples of such competitive, heterogeneous immunoassay systems are radioimmunoassays (RIAs), fluorescence immunoassays (FIAs) or enzyme immunoassays (EIAs), as well as enzyme-linked immunosorbent assays (ELISAs). The basic principle is the same in all these methods of detection. The most important difference is in the use of different labels. Heterogeneous immunoassays are very often performed by bringing together the individual reaction partners and reagents manually, separating the solid phase from the liquid one manually, and determining the amount of label, if necessary, after further washing and incubation steps.

The principle of an immunoassay, which is based on the displacement of one of the reaction partners of an immunological reaction by another, has been known from the technical literature (e.g., WO 91/13354). Mixing of the sample with the tracer (it is defined as an analyte or analyte derivative, to which one or more labeling elements are bound), which is necessary in competitive assays to start the competition reaction for the limited antigenic binding sites on the carrier, is eliminated in this displacement immunoassay. Separate reagent vessels or reagent layers along with the corresponding reagents are also eliminated in this displacement assay. The displacement takes place in a reaction column of a flow injection device. The analyte displaces during the reaction the tracer, which is labeled with, e.g., fluorophores, from its binding with the specific antibodies, which are bound to a matrix of the reaction column (i.e., the solid phase). Since no reagents are used in this embodiment, a fluorescence-measuring instrument must be used to quantitatively determine the amount of tracer molecules displaced. Since exactly one tracer molecule is displaced per molecule of analyte, there is a directly proportional relationship between the analyte concentration and the measured signal in displacement immunoassay. Even though an immunoassay using fluorophores as the labeling element makes it possible to obtain quantitative data on the reaction, it does require complicated and expensive measuring means, and is therefore unsuitable for performing a rapid screening on the spot for the presence of pollutants and for identifying their nature and amount.

Vessels have been known for performing the immunoassays, which are called microtiter plates and consist of a plurality of depressions arranged in a plastic card (e.g., DE 91 00 320 U1). These microtiter plates are coated with the antibodies or antigens prepared according to a complicated process. All further incubation and washing steps will subsequently take place in the above-mentioned depressions. However, this process, in which the reaction vessel also constitutes the carrier coated with the antibodies or antigens, has several disadvantages:

a) A microtiter plate normally consists of 96 depressions, which is meaningful for a larger serial investigation, but it represents a waste of material in the case of individual samples;

b) due to the fact that the depressions located adjacent to each other in the microtiter plate are normally coated with only one kind of antigen or antibody, rapid differential diagnosis of pollutants is possible only with difficulty;

c) the binding of the antigens and antibodies is again partially broken during the individual reaction steps, especially due to the intermediate rinsings, so that up to 70% of the original antigen-antibody complex may be lost. As a result, there is only a limited possibility of obtaining standardized and reproduced results;

d) the limited adsorption capacity of these plastic surfaces represents another disadvantage during the antigen or antibody loading of the microtiter plate.

Immunological test kits, e.g., pregnancy tests, in which small, dyed plastic particles ("latex beads") are used as labels on antibodies, have been known as well (e.g., DE-OS 40 37 736 or DE-OS 40 37 724). DE-OS 40 37 736 and DE-OS 40 37 724 each shown an example of a so-called sandwich-assay with a special aspect to dyed particles-sandwich-assays or bead-migration-assays or chronomatographic-strip-assays which are commonly used for pregnancy test procedures. DE'736 especially relates to a dip stick assay, whereas DE'724 concerns a migration-type test as disclosed on page 8, line 5 to page 9, line 4 of our description. The test carriers are special thin layers or membranes, which permit the "migration" of the antibodies thus labeled on the carrier layer toward another immunological binding partner. The driving forces of this migration include the capillary suction forces of the carrier material. The immunoassay principle of the test is the "non-competitive" assay. The antibody immobilized adsorptively or covalently on the solid phase can be reacted with a sample of unknown analyte concentration according to this process, which is generally also called "sandwich method," here specifically "dyed particles sandwich" assay, "bead migration" assay, or "chromatographic strip" assay. The two reaction partners are contacted via a migration process of the liquid phase with the dissolved analyte, or via the carrier. A second antibody (antibody conjugate), which is specific of the analyte and is also bound to a label, is added, and this second antibody will be bound to the analyte already fixed on the carrier. The intensity of the signal, which can now be evaluated optically, is an indicator of the amount of analyte in the sample. This antibody conjugate is preferably placed on the carrier, still in front of the zone with the covalently bound, unlabeled antibody. This antibody conjugate can thus be bound by the immobilized, unlabeled antibody after migration of the analyte together with it as antibody conjugate-antigen complexes. If no analyte is present in the sample, no visible complexes will form from antibody conjugate+immobilized antibody.

Such test methods have been established for larger multivalent or polyvalent analytes. However, these tests provide only qualitative measured results, which is sufficient and meaningful in the case of use as a pregnancy test or for determining infections in medical diagnostics. Qualitative measurement of smaller, environmentally relevant pollutant molecules and their quantitative determination are not possible in this manner.

WO 91/12528 discloses an immunoassay in the form of a test strip provided with a plurality of zones. To detect an analyte occurring in an aqueous solution, the test strip is dipped into this solution. The solution will then migrate through the strip due to capillary force, and reach first a first zone, which contains a first, labeled antibody that is specific of a first binding site of the analyte. The solution continues to migrate to a second zone, which contains a second antibody that is specific of a second binding site of the analyte. The sandwich consisting of the first antibody, the analyte, and the second antibody continues to migrate with the solution to a third zone, in which the sandwich is trapped, and the labeling of the first antibody is thus concentrated and thus made visible.

The disadvantage of this immunoassay is that two antibodies are needed for two different binding sites of the analyte. This is often impossible in the case of small analyte molecules.

FIG. 13 of the drawings shows schematically a process described in EP-PS 191 640, which operates with a test strip 100 consisting of absorbent material, on which a first antibody 102 is immobilized in a zone 101. One end of the test strip 100 is dipped into a test solution 103, which contains the analyte 104 to be determined and a second antibody 105, which is specific of the analyte 104. The first antibody 102 binds the complex consisting of the analyte 104 and the second antibody 105 during the capillary migration of the test solution 103 through the test strip 100. The complex bound to the first antibody 102 is dyed and detected as a result (not shown in FIG. 13) by means of a developing solution.

The disadvantage of this process is that two specific antibodies 102, 105 are needed.

The first antibody 102 must be able to distinguish between a second antibody 105 with and without bound analyte 104. This is hardly possible in the case of small analyte molecules (so-called monovalent antigens). A trapping zone 106 with immobilized analyte analog 107, in which zone the second, analyte-free antibody 105 is trapped to avoid indication error, is therefore additionally needed in this case on the test strip 100. The participating reaction partners must be made available in exactly defined amounts. Since a specific immunological reaction takes place between the second antibody 105 and the analyte 104 in the test solution, the reaction conditions must be controlled. All this makes the process complicated, expensive, and susceptible to failure. It can hardly be performed by laymen.

SUMMARY AND OBJECTS OF THE INVENTION

It is the primary object of the present invention to provide a process that requires only one antibody, in which both the procedure and the design of the testing device are simple and inexpensive, which permits reliable detection of even small analyte molecules, and can be performed on the spot even by laymen.

According to the invention, an immunological process is provided for determining an analyte in the sample wherein a test strip formed of an absorbent material is used, on which an antibody is immobilized in at least one partial area. The process includes bringing a test solution, which contains the sample and another reaction partner, into contact with one end of the test strip. The test solution is allowed to pass over at least one part of the test strip, including the partial area containing the antibody, by capillary migration. The test strip is subsequently washed and the test strip is brought into contact with a developing solution that contains members of a signal-generating system that is able to generate a detectable signal as a function of the amount of analyte in the sample in the partial area containing the antibody. The signal generator is then compared with a comparison standard. The antibody is specific of the analyte. An analyte analog is bound to the antibody. The affinity of the antibody for the analyte is higher than for the tracer. The other reaction partner is able to bind to the tracer. The tracer is displaced by the analyte during the capillary migration of the test solution. The signal generating system generates a signal with the tracer that has remained on the antibody and is bound to the other reaction partners.

The invention also provides a device for carrying out the process including a test strip formed of an absorbent material, on which an antibody is immobilized in at lease one partial area. A test solution containing the sample and another reaction partner and a developing solution, which contains members of a signal generating system that is able to generate a detectable signal as a function of the analyte in the sample on the partial area containing the antibody, is also provided. A comparison standard element is provided for comparison of the signals generated. An antibody specific to the analyte is provided as well as an analyte analog which is bound to the antibody. The other reaction partner is able to bind to the tracer. The signal generating system is provided for generating a signal with the tracer that is bound to the antibody and is bound to the other reaction partner.

The invention further involves an immunological process for determining an analyte in a sample wherein a test strip formed of absorbent material, in which an antibody is immobilized in at least one partial area, is used. The process includes bringing into contact a test solution containing the sample with one end of the test strip. The test solution is allowed to pass over at least one part of the test strip, including the partial area containing the antibody, by capillary migration. The signal generated is compared with a comparison standard. The antibody is provided to be specific for the analyte. An analyte analog (tracer) is bound to the antibody and the affinity of the antibody for the analyte is higher than for the tracer. A dye or dye generating or dye providing system that is able to bind to the tracer is present and the tracer is displaceable by the analyte during the capillary migration of the test solution.

The advantages of the present invention are as follows:

Only one antibody, which is specific of the analyte, is needed.

This antibody can also be prepared for small analyte molecules.

The process requires only one zone with immobilized antibody on the test strip; no trapping zone is necessary.

The antibody is saturated with tracer. In many cases, this stabilizes the antibody and permits long storage times.

No reaction takes place in the test solution. Controlled conditions are therefore not required for the test solutions.

Only the amount of a single antibody must be set; all the other reaction partners can be added in excess amounts, so that they do not have to be accurately quantified.

The antibody on the test strip in the process according to the present invention directly interacts with the analyte, i.e., the antibody and analyte are bound to each other without participation of a third partner. Contrary to this, the antibody on the test strip described in EP 191 640 B1 interacts only with a complex formed from the analyte and another antibody.

The immunological process according to the present invention along with the test device is characterized by sample migration (migration) and immunological displacement (displacement), and will hereinafter be called "migration-mediated immunodisplacement assay" (MIDA).

Commercially available membrane test strips of a great variety of pore sizes, e.g., Biodyne A, Biodyne B, Biodyne C, Immunodyne, Loprodyne, and Fluorotrans membranes, as well as membrane-"dipstick" laminates from the firm of Pall; cellulose nitrate BA83, BA85, and AE98; mixed cellulose esters ME28 and ME29; and cellulose acetate membranes from the firm of Schleicher & Schuell; Immobilon P from the firm of Millipore; and cellulose nitrate fabric from the firm of Sartorius can be used as the materials for the test strips used for the MIDA process.

The Immunodyne membrane permits direct, covalent binding of proteins, as a result of which these are irreversibly immobilized on the membrane. Immobilization of, e.g., antibodies on the other membranes by adsorption and/or the development of hydrophobic/hydrophilic interactions is also possible. The pores of the membranes are selected to be such that they form no or at most only weak diffusion barriers for the reactants or the substances present in the test.

A modified analyte is used as the tracer; the modification is selected such that the affinity of the antibody for the tracer is lower than for the analyte. This is the requirement for each molecule of analyte to indeed displace one tracer molecule from the antibody.

Another reaction partner present in the test solution is bound to the tracer, as a result of which the tracer is in turn able to generate a detectable signal after having been brought into contact with a developing solution. This may be a dyeing, or a radioactive or fluorescent signal. The signal on the test strip has its maximum (e.g., intense dyeing) when no analyte is present in the sample, because all tracer molecules remain on the antibody in this case.

If the analyte content in the sample is very high, all tracer molecules are displaced from the antibody, and the signal is zero (i.e., there is no dyeing).

If dyeing is selected as the signal, the other reaction partner may be, e.g., an enzyme conjugate that is able to be bind to the tracer. One component of the signal-generating system is in this case a substrate that is reacted by the enzyme into a dye. The other reaction partner must not bind to other components of the test system, e.g., the antibody, the analyte, or the material of the test strip, because this would distort the signal.

It is also possible to produce a dyeing by attaching dyed particles (e.g., latex beads) or dyed molecular complexes to the tracer or the other reaction partner. Radioactive or fluorescent labeling is also possible in this manner. The procedure can be carried out without developing solution and the signal-generating system in this case.

If, e.g., the tracer is visualized directly with an attached dye (molecule or particle), the area of the test strip containing the antibody is visible as a dyed area even before the beginning of the test. The other reaction partner is eliminated. If part of the tracer is displaced by the analyte in the course of the test, in which only one end of the test strip must be dipped into the solution containing the sample to be investigated, the dyeing migrates with the capillary migration of the test solution. The migrated dyeing is removed by washing out, and the amounts of analyte detected can be inferred from the reduction of dyeing of the area containing the antibody. Treatment of the test strip with a developing solution is eliminated in this embodiment of the test.

If a dye is bound to the other reaction partner, this must be present in the test solution together with the sample. The dyeing now migrates through the strip with the test solution. Depending on the amount of the analyte, part of the dyeing is immobilized in the area containing the antibody, and the rest of the dyeing can be removed by washing. The degree of dyeing is again an indicator of the amount of analyte detected.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3a is a view of a test strip prior to testing;

FIG. 3b is a view of a test strip with one end inserted in a test solution;

FIG. 3c is a test strip during the step of washing the test strip;

FIG. 3d is a test strip immersed in developing solution;

FIG. 3e is a view of a plurality of different test strips having differently colored measurement areas, and a view of a color scale;

FIG. 3F is a symbol indicating a water faucet for a rinsing step;

FIG. 3G is one embodiment of a color comparison standard;

FIGS. 8A–8C are a view of a plurality of test strips of the type shown in FIG. 2f with different colored measurement areas;

FIG. 8D is another embodiment of a color comparison standard;

FIGS. 9A–9C are a view of a plurality of test strips of the type shown in FIG. 2g with different colored measurement areas;

FIG. 9D is another embodiment of the color comparison standard;

FIG. 10a is a test kit;

FIG. 10b is a chamber closure with a suction device and a test strip;

FIG. 1a shows a schematic representation of a test strip 1 consisting of an absorbent material, on which antibody molecules 3 are immobilized in a measurement area 2. The area 2 may be in the form of, e.g., a spot, a line, or a symbol. Tracer molecules 4, which consist of the analyte 5 and an appendage 6 (e.g., biotin), are bound to the antibody molecules 3.

In FIG. 1b, the lower end of the test strip 1 is dipped into a vessel 7 containing test solution 8. The test solution contains the analyte 5 and another reaction partner 9 (e.g., a streptavidin-enzyme conjugate). The test solution is absorbed through the test strip by capillary forces. A suction device 10 (e.g., a sponge) at the top end of the test strip makes it possible to absorb a larger amount of liquid than would be possible with the test strip alone.

Figure 1A:
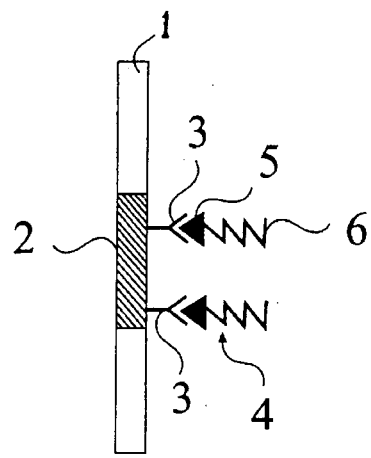
FIG. 1a is a view of a test strip.
Figure 1B:
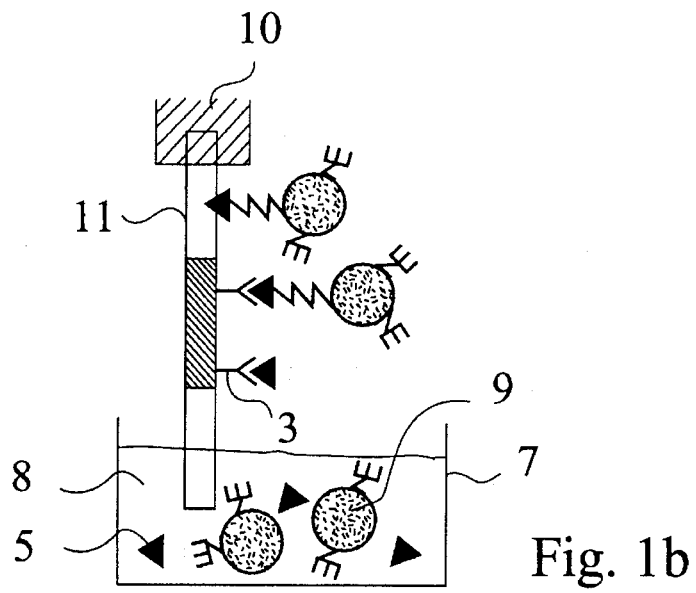
FIG. 1b is a view of a test strip applied into a vessel containing test solution.

Since the antibody 3 has a higher affinity for the analyte 5 than for the tracer 4, each molecule of analyte 5 displaces one tracer molecule 4. The other reaction partner 9 is bound to the tracer at the same time. The displaced tracer 4 migrates with its reaction partner 9, which is bound to it, into the area 11 of the test strip 1 that is located above the measurement area 2 containing the antibody 3. The displaced tracer 4 is removed by washing the test strip 1 with, e.g., water (not shown in FIG. 1).

The signal-generating system 9, 14 in this example consists of two components: On the one hand, the other reaction partner 9, which in turn consists of a conjugate of streptavidin molecule 16 and two enzyme molecules 15, and, on the other hand, of a substrate molecule 14, which is present in a developing solution 13.

Figure 1C:
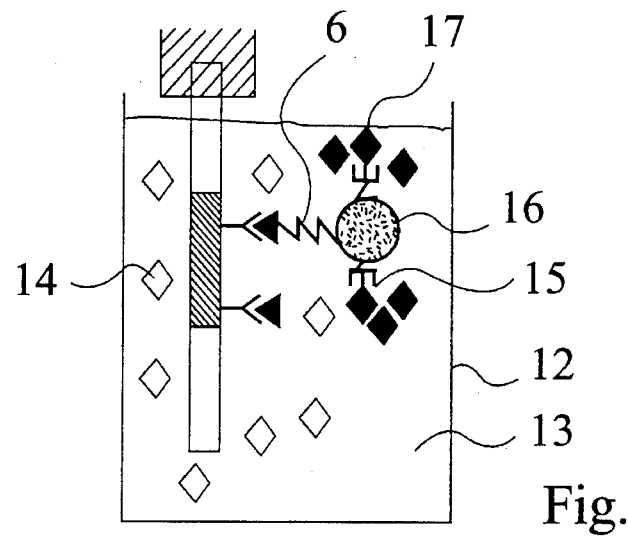
FIG. 1c is a view of a washed test strip dipped into a vessel containing developing solution.

The washed test strip 1 is dipped into a vessel 12 containing the developing solution 13 in FIG. 1c. The substrate molecules 14 enter the test strip 1 with the developing solution 13. If enzyme 15, which is bound, together with streptavidin 16, to the biotin 6 of the tracer 4, and substrate 14 meet, a dye 17 is formed from the substrate 14 in an enzymatic reaction. As a result, all the tracer molecules 4 having remained on the test strip 1 are labeled with dye. The amount of the analyte 5 in the sample can be inferred from the intensity of the dyeing.

FIG. 2 shows possible embodiments (A through G) of the MIDA test strip for determining an analyte. The meanings of the reference numerals are as follows:

| | |
|---|---|
| 18 | labeling field or contact area to the suction device 10. |
| 2, 2.6–2.10 | immobilized antibody or antigen or tracer, placed in various arrangements corresponding to the requirements of the possible test evaluation, |
| 2.1–5 | variant of embodiment A, in which the immobilized antibodies or antigens or the tracer 2 have different specificities, affinities, origins, compositions, or concentrations. |
| 1 | Membrane as a test strip carrier or membrane component in the case of plastic laminates (dipsticks). |
| 19 | Immobilized antibody, different from 2, for the tracer displaced in the MIDA test. This arrangement makes possible the direct, proportionate assignment of the sample analyte to the optically visible change in the color of the strip in this zone of the membrane; shown in detail in FIG. 8. |
| 20 | Immobilized antibody, which is different from 2 and 19 and is specific of a component that is different from the tracer and the analyte, but is always present in the MIDA test, e.g., the avidin- or streptavidin-enzyme complex. |

Dinitrophenyl-lysine (DNP-L) was used in the following examples. However, the present invention is not limited to this substance. All low-molecular-weight substances, against which the antibodies are formed directly or indirectly, may be used as the analyte. The monoclonal anti-dinitrophenol antibody described by Stanley et al. (1983)[1] was used as the specific antibody. The individual steps for preparing the tracers (streptavidin-biotin systems), as well as the described enzymatic detection reactions of the antibody binding (alkaline phosphatase and peroxide reactions), have been known from the state of the art.

[1]Stanley, C., A. M. Lew, and M. W. Steward (1983): The measurement of antibody affinity: A comparison of five techniques utilizing a panel of monoclonal anti-DNP antibodies and the effect of high affinity antibody on the measurement of low affinity antibody. *J. Imm. Methods*, Vol. 64, pp. 119–132.

EXAMPLE 1

Figure 2A:
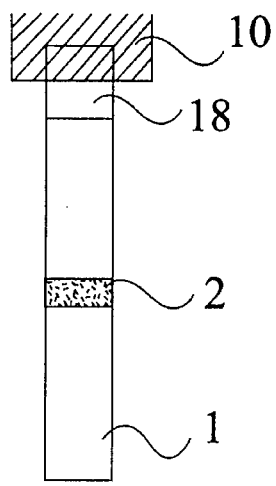
FIG. 2a is a test strip having a single measurement area.
Figure 2B:
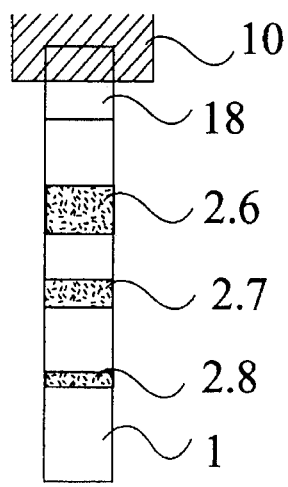
FIG. 2b is a test strip having a plurality of measurement areas of different thicknesses.
Figure 2C:
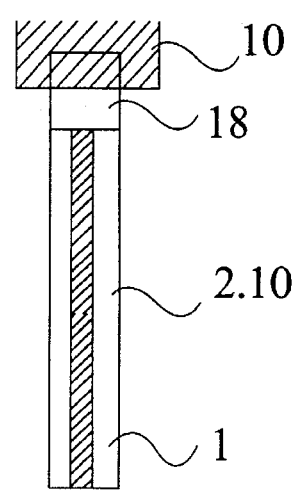
FIG. 2c is a test strip having a test strip extending along a length of the test strip and substantially parallel to a direction of absorption of the test solution.
Figure 2D:
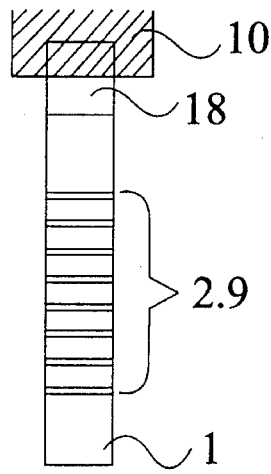
FIG. 2d is a test strip having a plurality of measurement areas of substantially equal thickness and substantially uniformly spaced.
Figure 2E:
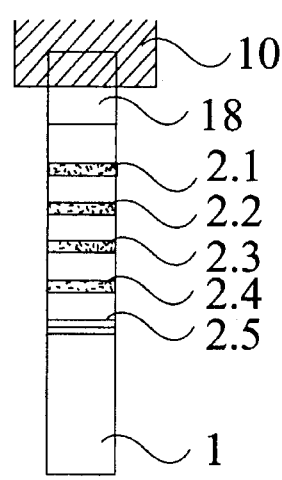
FIG. 2e is test strip having a plurality of measurement areas with different specificities, affinities, origins, compositions or concentrations.

Preparation of a Membrane Carrier Coated with Anti-Dinitrophenyl-Lysine Antibodies for the MIDA Test The antibodies, in the form of a buffered solution (suitably 1 mg/mL), are applied as a linear area to the membrane to be used. For example, Linomat IV (firm of Camag) is suitable for this purpose. This yields, e.g., 0.5 μg of protein per membrane test strip (FIG. 2A). The shape of the linear application offers decisive advantages: a) It leads to marked savings of materials; b) by repeatedly coating the same line, it is possible to concentrate the material applied; c) uniform coating of the test strip batches can also be performed in a reproducible manner; and d) unambiguous evaluation of the measured value is facilitated, because application in a linear form is favorable for assignment to a predetermined color or length scale. The membrane is subsequently dried in air at room temperature (ca. 22°–25° C.). The still free binding sites on the test strip are blocked by incubating the membrane in saturating reagents.

Prior-art saturating reagents are, e.g., 3% (w/v) bovine serum albumin (BSA) in a phosphate-buffered solution (PBS);

5% (v/v) equine serum (ES) in PBS;

0.25% (w/v) casein (firm of Merck)+0.1% (v/v) Triton X-100 (firm of Rohm & Haas) in PBS. PBS: 0.15 moles/L NaCl, 0.008 moles/L $Na_2HPO_4$, 0.002 moles/L $NaH_2PO_4$, pH=7–8.

The saturation step is followed by a washing step with 0.1% (v/v) Tween 20 (firm of Merck) in a PBS solution to remove excess saturating reagent.

This is followed by incubation with the tracer, which is added in excess in relation to the immobilized antibody in order to saturate all possible antigen binding sites on the antibodies. Chemically modified DNP-lysine, with which D-biotin-epsilon-amidocaproic acid hydroxysuccinimide ester (firm of Boehringer Mannheim) was covalently coupled, is used as the tracer, as a result of which the tracer is again able to specifically react with avidin- or streptavidin-enzyme conjugates and to form a very stable bond. After incubating the antibodies with DNP-lysine-biotin, another washing step is performed in a Tween/PBS solution, as was described above. The membrane carrier thus prepared is subsequently dried in air as described, and it can be used directly in the MIDA test or stored in a stable form.

EXAMPLE 2

MIDA Test with Dinitrophenyl-Lysine as the Analyte

The schematic representation of the test procedure with a test strip (prepared according to Example 1, FIG. 2A) is shown in FIG. 3. The meanings of the reference numerals are as follows:

10 Holding and/or suction device, which is provided with the test strip, e.g., absorbent cotton or nonwoven material.
21 Indication of the direction in which the liquid is transported over and/or through the membrane carrier due to capillary suction forces.
22 Water faucet symbol: It represents a laboratory wash bottle, water faucet, or another, not specifically defined device for washing/rinsing the test strip.
23 Color comparison standard supplied with the test kit or attached to the testing device for the quantitative evaluation of the degree of change in color.

The membrane test strip 1 prepared is already introduced into the suction device 10 (FIG. 3A). The suction device shall guarantee the capillary transport of liquid over the membrane after the latter has been completely wetted. The membrane carrier with the holder can then be placed in, e.g., the lid of a test kit (FIG. 10). The solution containing the analyte (DNP-lysine) is subsequently transferred into the sample vessel (not shown here). A defined amount of avidin—preferably streptavidin-enzyme conjugate—is already present in the sample vessel (in the freeze-dried form or as a buffered solution). Enzymes suitable for use for this purpose, e.g., alkaline phosphatase, peroxidase,β-galactosidase, glucose oxidase, luciferase, have been known from the state of the art, but the suitable enzymes are not limited to these alone. The membrane strip 1 is now placed into the sample vessel such that the lower edge of the strip just dips into the sample solution (FIG. 3B). The capillary transport of the liquid of the sample solution with the analyte and enzyme conjugate now begins over or through the membrane. The immunological displacement reaction between the tracer and the analyte now takes place in the intended area 2; the analyte is bound, and the displaced tracer is transferred into the suction device 10 with the liquid due to the capillary suction forces. After a predetermined time, or when the total amount of sample liquid has been absorbed, the membrane strip 1 is removed from the sample vessel and rinsed, e.g., under a water faucet 22 or with a laboratory wash bottle (FIG. 3C). The test strip is subsequently completely wetted with the liquid (e.g., by dipping in completely or by shaking the vessel) in a second vessel (substrate vessel, FIG. 10), which contains the corresponding substances in the freeze-dried form (FIG. 3D).

When freeze-dried substances are used, these are first rehydrated with a specified amount of, e.g., water. The substrate buffers are always adapted to the corresponding enzyme conjugate. The composition for alkaline phosphatase is listed below as an example:

| Substrate buffer: | 0.1 moles/L NaHCO$_3$, 0.001 moles/L MgCl$_2$, 0.7 mmoles/L NBT, 0.3 mmoles/L BCIP, pH = 9.8. |
|---|---|

BCIP: 5-bromo-4-chloro-3-indolyl phosphate disodium salt
NBT: 2,2'-di-p-nitrophenyl-5,5'-diphenyl-3,3'-(3,3'-dimethoxy-4,4'-diphenyl) ditetrazolium chloride.

After a specified reaction time (e.g., 1 to 2 minutes), the reaction is stopped by, e.g., rinsing the test strip with water, or rapidly drying the test strip, and the change in color achieved is compared with the color scale 23 for evaluation (FIG. 3E). The intensive dyeing (FIG. 3E, left) indicates that the sample contains no analyte, or that it contains an amount below the detection limit for this test, as a consequence of which displacement of tracer did not occur. The absence of color development (FIG. 3E, right) indicates complete displacement of the tracer and consequently a high analyte content in the sample solution. The middle part of FIG. 3E represents a possible intermediate step depending on the analyte concentration during the change in color. The color intensity is inversely proportional to the analyte concentration measured in this example.

EXAMPLE 3

Embodiments and Possibilities of Evaluation of the MIDA Test

The schematic representation of some embodiments of MIDA test strips and possibilities of evaluation are shown in FIGS. 4, 5, 6, 7, 8, and 9. The meanings of the reference numerals are as follows:

| 23 | Color comparison standard supplied with the test kit or attached to the testing device for the quantitative optical evaluation of the MIDA test. |
|---|---|
| 23.1, 23.2, 23.4 | Variants of the color comparison scale 23 |
| 23.3 | Variants of the scale for the evaluation of the test, which is based on the determination of the length of the dyed or decolorized areas after the MIDA test. |
| A B C: | Developed test strips with A: very low analyte content in the sample, B: medium analyte content, and C: very high analyte content. |

Figures 4A, 4B, 4C, 4D:
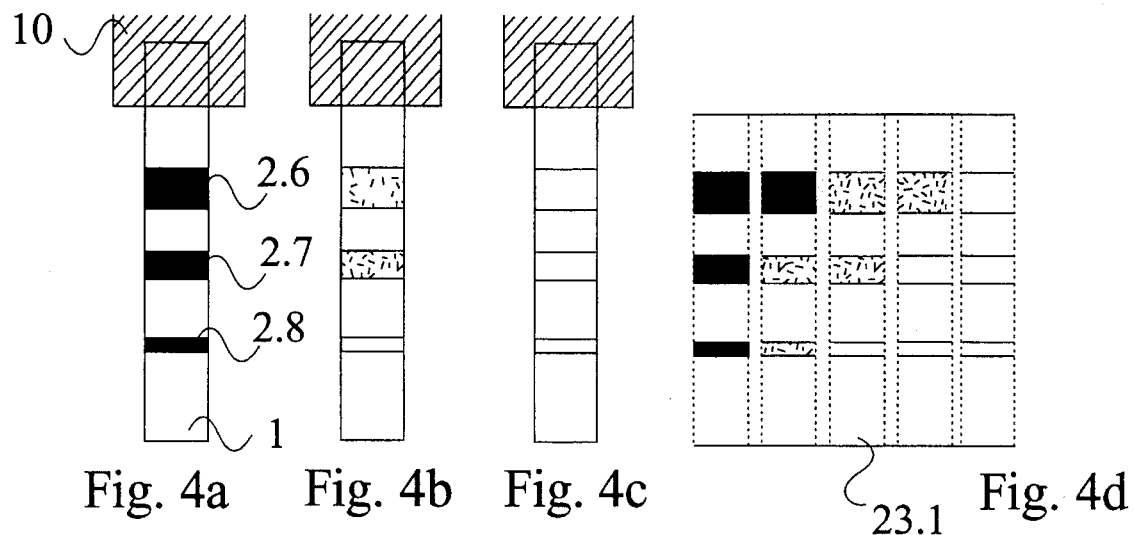
FIGS. 4A–4C are a view of a plurality of test strips of the type shown in FIG. 2b with different colored measurement areas.
FIG. 4D is another embodiment of a color comparison standard.

The test strips represented in FIGS. 2 through 9 are prepared analogously to Example 1. The test is performed in exactly the same manner as described in Example 2. FIG. 4 shows the possible evaluation of test strips (FIG. 2B) in which the reaction zone is applied to the membrane in areas of different widths 2.6–2.8. It was observed that the change in the width of the dyed field permits a finer gradation of individual shades of color/tones and thus permits more accurate quantification of the measurement.

Figures 5A, 5B, 5C, 5D:
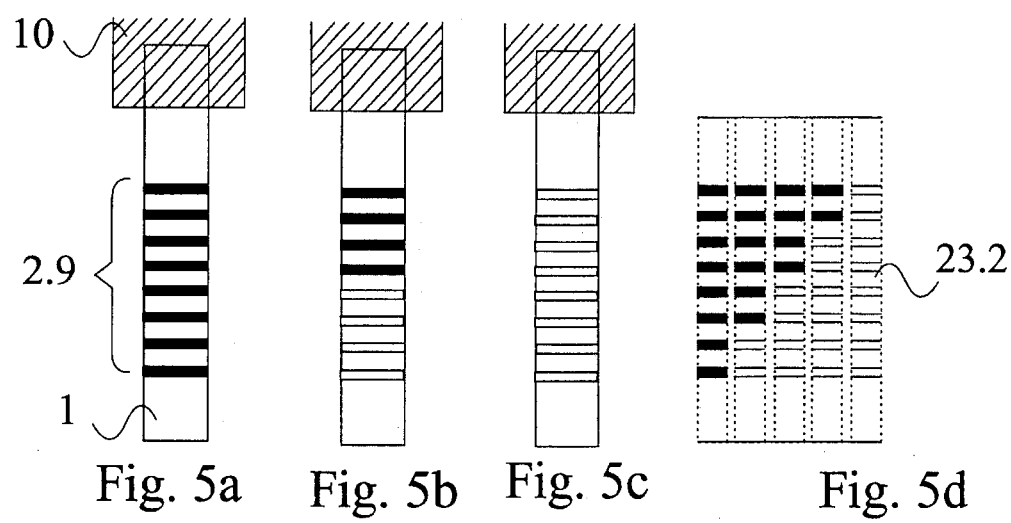
FIGS. 5A–5C are a view of a plurality of test strips of the type shown in FIG. 2d with different colored measurement areas.
FIG. 5D is another embodiment of a color comparison standard.
Figures 6A, 6B, 6C, 6D:
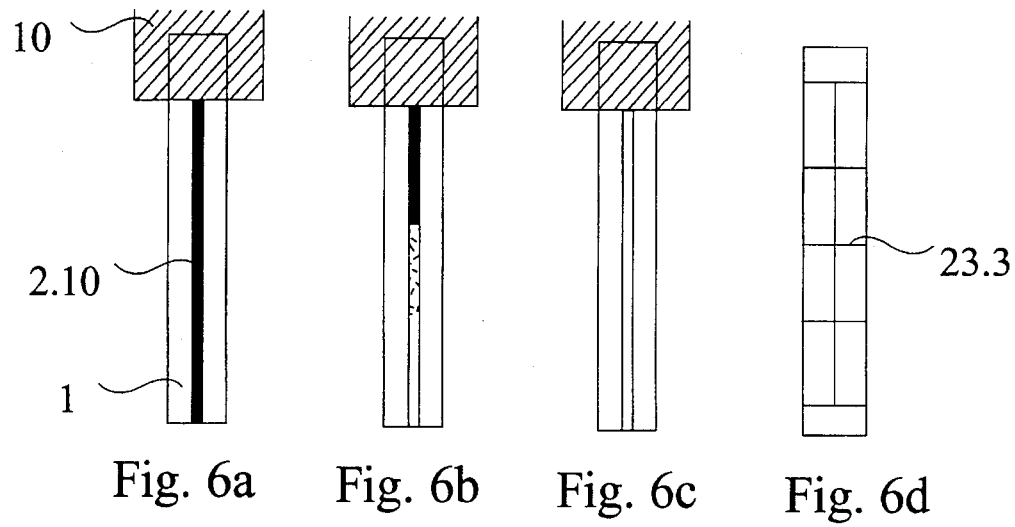
FIGS. 6A–6C are a view of a plurality of test strips of the type shown in FIG. 2c with different colored measurement areas.
FIG. 6D is another embodiment of a color comparison standard.

Higher accuracy is also achieved by performing the test as described in FIG. 5. A unit that can be evaluated optically with greater ease and higher accuracy is obtained by applying individual linear areas 2.9 spaced at specified distances from one another, compared with a completely charged membrane. The individual transitions between the membrane and the reaction zone are also advantageous for a possible quantitative scale division. Performing the test with an area 2.10 arranged in the longitudinal direction of the test strip 1, as shown in FIG. 6, makes it possible to quantify the test without color comparisons. The evaluation is performed here by determining the lengths of individual areas 2.10 on the test strip. Dyed or decolorized areas indicate the concentration of the analyte in the test based on the length on the strip. The concentration is read by placing a graduated scale 23.3 adjacent to or over the test strip.

Figures 7A, 7B, 7C, 7D, 7E:
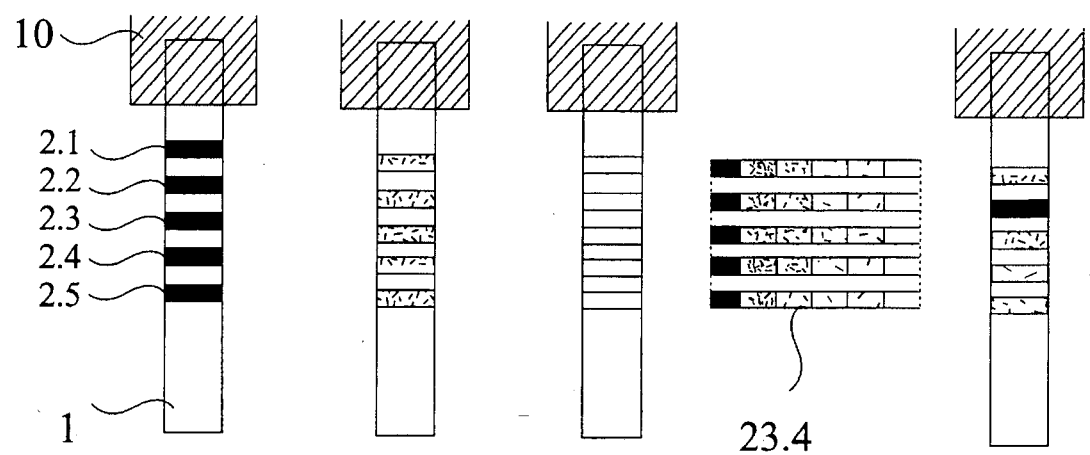
FIGS. 7A–7D are a view of a plurality of test strips of the type shown in FIG. 2e with different colored measurement areas.
FIG. 7E is another embodiment of a color comparison standard.

FIG. 7 shows schematically the evaluation with a "Multianalyte" test strip, e.g., for indicating different analytes in one sample. The individual areas 2.1–2.5 contain an antibody each that is specific of another analyte. The color comparison scales 23.4 permit direct quantification and assignment of the signals to individual analytes (FIG. 7D).

Figure 2F:
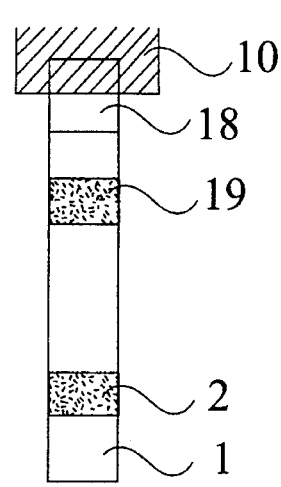
FIG. 2f is a test strip with a first measurement area preferably binding to an analyte and a second measurement area preferably binding to a tracer.

FIG. 8 shows a test design and evaluation variant, in which the amount of analyte in the sample is proportionate to the dyeing, i.e., the color intensity increases with increasing amount of analyte. In addition to the tracer-saturated antibody in the lower area 2 of the strip, a second zone 19 containing specific anti-tracer antibodies is placed (FIG. 2F).

These second antibodies of equal specificity considerably differ from the first ones in terms of their affinity due to the fact that they preferably bind the tracer and do not permit displacement by the analyte. Furthermore, these antibodies are not saturated with tracer for the purpose of the test. The tracers displaced in the lower area 2 of the strip are thus again bound specifically in the upper area of the strip 19 during the test reaction, and they are indicated by, e.g., an enzymatic reaction and can be quantified by means of a color comparison standard.

Figure 2G:
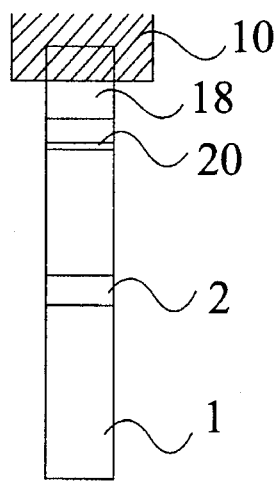
FIG. 2g is a test strip with a first measurement area preferably binding to an analyte and a second measurement area preferably binding to a component different than the analyte but always present in the test solution.

The test design according to the present invention always makes it possible to integrate an internal test control. This is shown in FIG. 9 as an example. An additional, narrow zone 20 containing antibodies is placed on the test strip 1 in its upper area (FIG. 2G). These antibodies are specific of a component that is different from the tracer 4 and the analyte 5, but is always present in the test, e.g., the avidin- or streptavidin-enzyme complex 9. A control for the absorption behavior of the membrane, the migration of the test components, the quality of color development, i.e., the enzyme activity as well as the corresponding reagents and the immobilized antibodies, is thus formed in each test. The color signal visible at the top edge of the strip in zone 20 does not depend on the analyte.

EXAMPLE 4

Embodiment of the MIDA Test Kit

FIG. 10A shows as an example a possible embodiment of a test kit. The kit consists of a vessel 24 with two separate chambers, one of which is used as the MIDA reaction chamber 25, and the second chamber 26 contains the substrate buffer for the color development. The color comparison standards 23 and scales are applied to the wall of the vessel. Both chambers are provided with closures 27, 28, and one of these closures contains the holding or suction device 10 for the test strips. FIG. 10B shows a chamber closure 27 threaded cover with the suction device 10 together with the test strip 1 after a measurement.

Figure 11A:
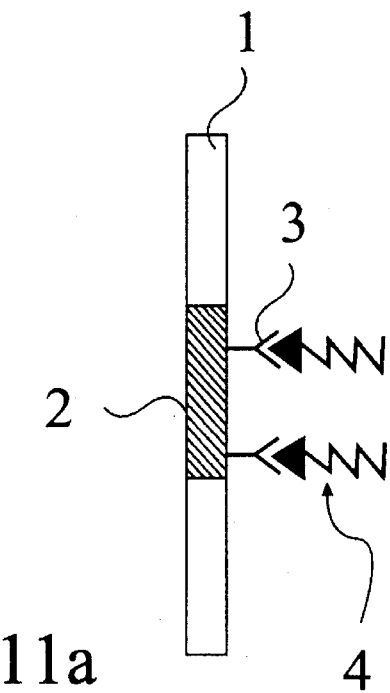
FIG. 11a is a test strip according to another aspect of the invention.
Figure 11B:
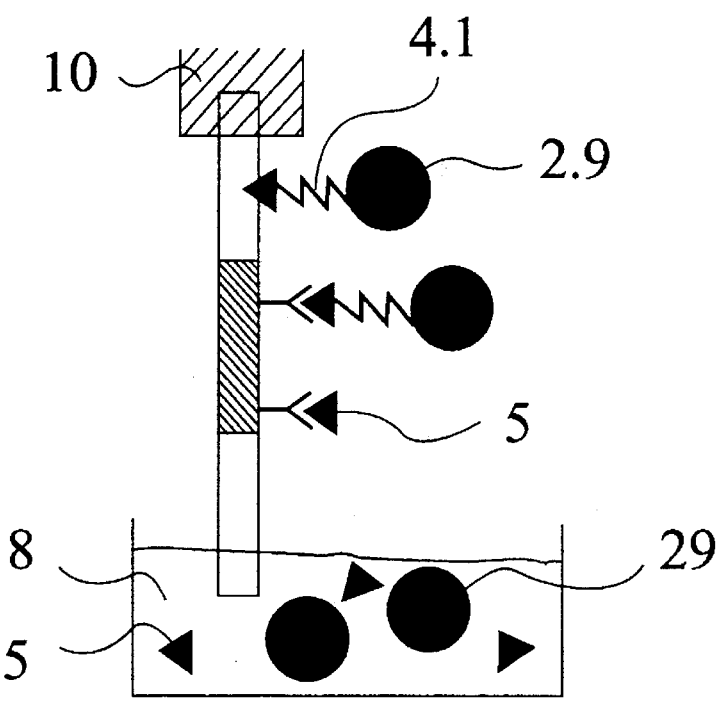
FIG. 11b is the test strip of FIG. 11a in contact with a test solution containing dye.

FIG. 11 (11a: dry test strip, 11b: measurement) shows schematically the principle of operation of a process according to one aspect of the invention, in which a dye 29 (molecules or particles) is present in the test solution 8 and is absorbed into the test strip 1 together with the analyte 5 during the test. The dye 29 is bound to the tracer 4 and renders same visible. Displaced tracer 4.1 is washed off, and the dyeing of the area 2 containing the antibody indicates the amount of analyte. Development of the dyeing is not necessary.

Figure 12A:
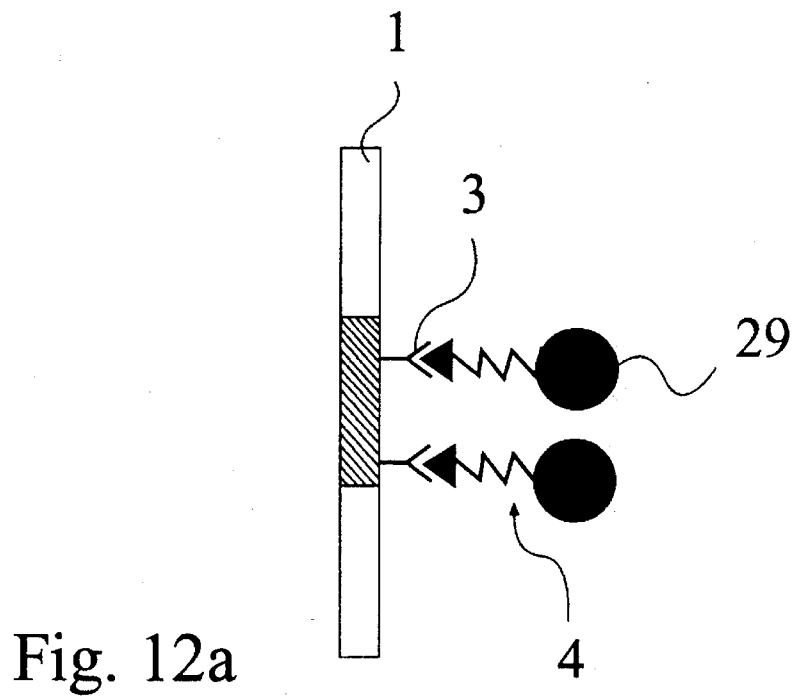
FIG. 12a is a test strip according to still another object of the invention.
Figure 12B:
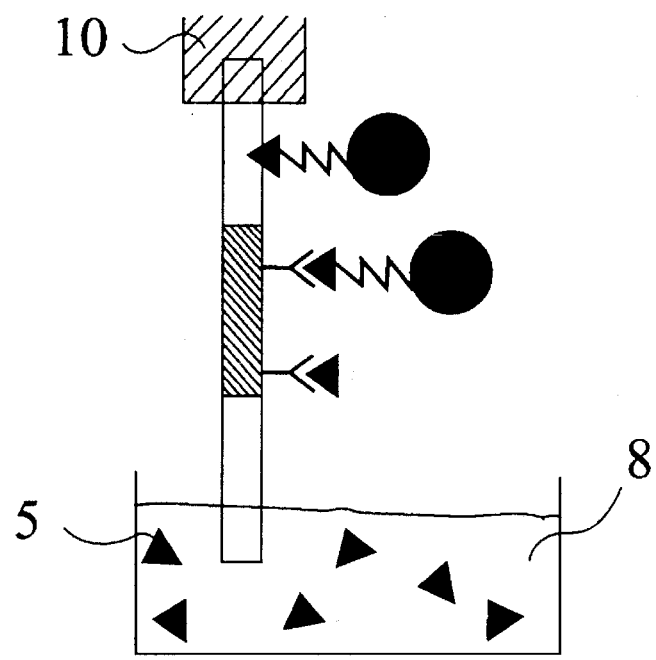
FIG. 12b is a test strip of FIG. 12a in contact with a test solution.
Figure 13A:
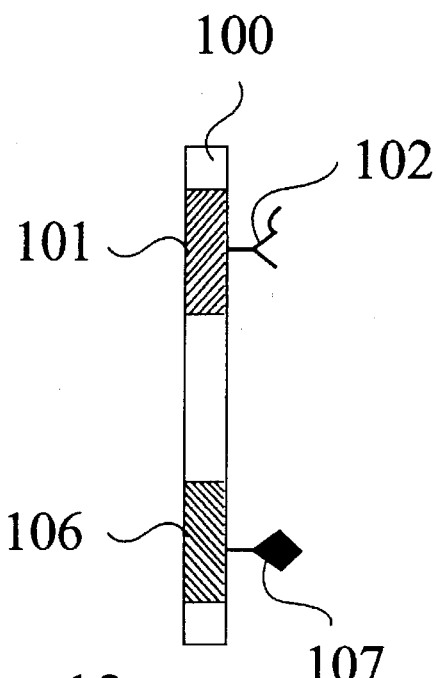
FIG. 13a is a test strip according to the state of the art.
Figure 13B:
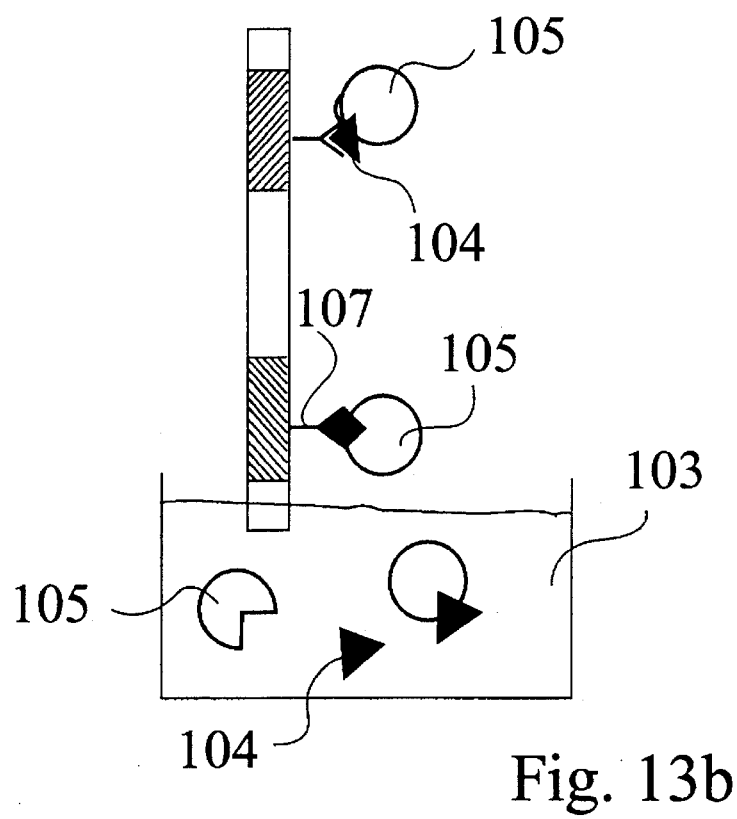
FIG. 13b is a test strip of FIG. 13a in contact with a test solution of the prior art.

The dye 29 is already bound to the tracer 4 on the dry test strip (FIG. 12a) in FIG. 12. The test solution 8 needs to contain only the analyte 5.

While specific embodiments of the invention have been shown and described in detail to illustrate the application of the principles of the invention, it will be understood that the invention may be embodied otherwise without departing from such principles.

What is claimed is:

1. An immunological process for determining a concentration of an analyte in a sample, the process comprising the steps of:

providing a test strip with an antibody which is specific to the analyte, said test strip being formed of porous material including a measurement area spaced from one end of said test strip, said antibody being bound and immobilized to said test strip in said measurement area, said antibody being bound to an analyte analog (tracer), said antibody having a higher affinity for the analyte than said analyte analog (tracer);

providing a test solution including the sample, said test solution including a reaction partner being an enzyme conjugate bindable to said analyte analog (tracer);

bringing said one end of the test strip into contact with said test solution to cause said test solution to move through said test strip and through said measurement area by capillary migration, said moving of said test solution through said measurement area causing any analytes present in the test solution to displace said analyte analog (tracer) from said measurement area;

removing said test strip from said test solution;

washing said test strip after said removing from said test solution to remove said displaced analyte analog (tracer);

bringing said test strip into contact with a developing solution for enzyme reactions, said developing solution including members of a signal-generating system able to generate a detectable signal as a variation in color of said measurement area as a function of a concentration of the analyte in the sample, said detectable signal being generated by an enzyme reaction between said developing solution and said analyte analog (tracer) remaining on said antibody in said measurement area with said reaction partner bound to said analyte analog (tracer);

comparing said detectable signal from said measurement area with a comparison standard relating different variations in colors of said detectable signal with a concentration of the analyte in the sample;

detecting which of said different colors of said comparison standard said detectable signal most closely matches in order to determine the concentration of the analyte.

2. Process in accordance with claim 1, wherein:

said antibody is immobilized by covalent interactions.

3. Process in accordance with claim 1 wherein:

said test strip is formed of nonwoven paper or membrane materials with or without plastic carrier material being used.

4. Process in accordance with claim 1, wherein:

said analyte is a low-molecular-weight pollutant from soil, air or water samples.

5. Process in accordance with claim 1, wherein:

said change in color is brought about enzymatically by reacting dye precursors by means of said signal-generating system.

6. Process in accordance with claim 1, wherein:

a color chart displaying various color shades which are assigned to the defined analyte concentrations, is used as said comparison standard.

7. Process in accordance with claim 1 wherein:

said antibody is applied to said test strip in the form of one or more parallel lines extending at right angles to the direction of the capillary migration of the test solution.

8. Process in accordance with claim 1, wherein:

said antibody is applied to said test strip in the form of a plurality of parallel lines extending at right angles to the direction of the capillary migration of the test solution or as a continuous area extending in the direction of the capillary migration of the test solution, and a length of an area whose color has changed on the test strip is also considered to be an indicator of the analyte concentration in the sample.

9. Process in accordance with claim 1, wherein:

specific antibodies specific to different analytes are applied in a plurality of measurement areas on said test strip.

10. Process in accordance with claim 1, wherein:

a second measurement area containing another antibody in an immobilized form is provided on said test strip behind said measurement area containing the antibody when viewed in the direction of the capillary migration of the test solution, said another antibody is specific of a reaction component that is always present in the test solution and is different from the tracer and the analyte, said another antibody forming a test reaction for internal test control, said another antibody not being present either in the test solution or bound on said measurement area.

11. Process in accordance with claim 1, wherein:

said antibody is immobilized by adsorptive interactions.

12. Process in accordance with claim 1, wherein:

said antibody is immobilized by hydrophobic/hydrophilic interactions.

13. An immunological process for determining a concentration of an analyte in a sample, the process comprising the steps of:

providing a test strip with an antibody which is specific to the analyte, said test strip being formed of porous material including a measurement area spaced from one end of said test strip, said antibody being bound and immobilized to said test strip in said measurement area, said antibody being bound to an analyte analog (tracer), said antibody having a higher affinity for the analyte than said analyte analog (tracer);

providing a test solution including the sample;

providing dyed particles in said test solution, said dyed particles being bindable to said analyte analog (tracer) and able to generate a detectable signal as a function of the concentration of the analyte;

bringing said one end of the test strip into contact with said test solution to cause said test solution to move through said test strip and through said measurement area by capillary migration, said moving of said test solution through said measurement area causing any analytes present in the test solution to displace said analyte analog (tracer) from said measurement area;

moving said dyed particles into contact with said measurement area and analyte analog (tracer) to bind said dyed particles to said analyte analog (tracer) bound to antibodies in said measurement area and generate said detectable signal in said measurement area;

comparing said detectable signal in said measurement area with a comparison standard relating variations in colors of said detectable signal with a concentration of the analyte in the sample;

detecting which of said different colors of said comparison standard said detectable signal most closely matches in order to determine the concentration of the analyte.

\* \* \* \* \*